US009283124B2

(12) United States Patent
Hashimoto et al.

(10) Patent No.: US 9,283,124 B2
(45) Date of Patent: Mar. 15, 2016

(54) WEARING ARTICLE
(71) Applicant: UNICHARM CORPORATION, Shikokuchuo-shi, Ehime (JP)
(72) Inventors: Tatsuya Hashimoto, Kanonji (JP); Tetsuo Okubo, Kanonji (JP)
(73) Assignee: UNICHARM CORPORATION, Ehime (JP)
(*) Notice: Subject to any disclaimer, the term of this patent is extended or adjusted under 35 U.S.C. 154(b) by 0 days.
(21) Appl. No.: 14/404,976
(22) PCT Filed: Sep. 17, 2013
(86) PCT No.: PCT/JP2013/005481
§ 371 (c)(1),
(2) Date: Dec. 2, 2014
(87) PCT Pub. No.: WO2014/050014
PCT Pub. Date: Apr. 3, 2014

(65) Prior Publication Data
US 2015/0164708 A1 Jun. 18, 2015

(30) Foreign Application Priority Data

Sep. 28, 2012 (JP) ................................ 2012-218690
Jul. 5, 2013 (JP) ................................ 2013-142160

(51) Int. Cl.
*A61F 13/15* (2006.01)
*A61F 13/49* (2006.01)
(Continued)

(52) U.S. Cl.
CPC .......... *A61F 13/49017* (2013.01); *A61F 13/496* (2013.01); *A61F 13/4942* (2013.01); *A61F 2013/49042* (2013.01); *A61F 2013/49092* (2013.01)

(58) Field of Classification Search
CPC ........... A61F 13/49413; A61F 13/4942; A61F 2013/49042; A61F 2013/49088; A61F 2013/49092

USPC ........................................ 604/385.26, 385.27
See application file for complete search history.

(56) References Cited

U.S. PATENT DOCUMENTS 4,808,177 A * 2/1989 DesMarais et al. ...... 604/385.27
7,955,311 B2 * 6/2011 Tanaka et al. .............. 604/385.3
(Continued)

FOREIGN PATENT DOCUMENTS

| JP | 2002-273808 A | 9/2002 |
| JP | 2010-279612 A | 12/2010 |
| JP | 2011-240054 A | 12/2011 |

OTHER PUBLICATIONS

International Search Report mailed Dec. 24, 2013 in International Application No. PCT/JP2013/005481 filed Sep. 17, 2013.
(Continued)

*Primary Examiner* — Lynne Anderson
(74) *Attorney, Agent, or Firm* — Hauptman Ham, LLP

(57) ABSTRACT

In a wearing article including front and rear waist panels and a crotch panel, a pair of leg sheets including backing sheets and leg elastics attached under tension between two layers of the respectively doubled up backing sheets extends along lateral edge portions of the crotch panel, and distal end portions of the leg sheets are attached to respective skin-facing surfaces of the front and rear waist panels through first and second joint regions. In this way, the pair of leg sheets has an elastically contractible region between the first and second joint regions and elastically relaxed regions in end portions located outboard of the first and second joint regions in a longitudinal direction, and the elastically relaxed regions are formed on surfaces thereof with gathers.

4 Claims, 10 Drawing Sheets

(51) Int. Cl.
*A61F 13/494* (2006.01)
*A61F 13/496* (2006.01)

(56) References Cited

U.S. PATENT DOCUMENTS

2011/0251576 A1* 10/2011 Ando et al. .............. 604/385.16
2012/0143162 A1   6/2012 Mukai et al.
2012/0311771 A1* 12/2012 Ichikawa et al. ................. 2/401
2013/0041340 A1   2/2013 Kawakami et al.
2015/0032072 A1*  1/2015 Hashimoto et al. ...... 604/385.21

OTHER PUBLICATIONS

Written Opinion mailed Dec. 24, 2013 in International Application No. PCT/JP2013/005481filed Sep. 17, 2013.

* cited by examiner

WEARING ARTICLE

RELATED APPLICATIONS

The present application is a National Phase of International Application Number PCT/JP2013/005481, filed Sep. 17, 2013, which claims priority to Japanese Application Number 2012-218690, filed Sep. 28, 2012 and Japanese Application Number 2013-142160, filed Jul. 5, 2013.

TECHNICAL FIELD

The present disclosure relates to wearing articles, more particularly to wearing articles such as pants-type diapers, toilet-training pants or incontinent pants.

BACKGROUND

Various methods of manufacturing elastic composite sheets to be used as components in wearing articles are known. For example, JP 2002-273808 A (PTL 1) discloses a method of manufacturing an elastic composite sheet including the steps of attaching elastics such as rubber strings to a sheet of, for example, a nonwoven fabric or a plastic film, and cutting these elastics to form elastic regions and inelastic regions in the elastic composite sheet for making a disposable diaper using this elastic composite sheet.

CITATION LIST

Patent Literature

{PTL 1}: JP 2002-273808 A

SUMMARY

Technical Problem

In the elastic sheet disclosed in PTL 1, along the direction in which a continuous sheet web runs, adhesive distributed regions and adhesive-free regions are alternately formed on the sheet web, and the elastics are cut in the adhesive-free regions, i.e., snapped back to form inelastic regions. In consequence, the elastics cut in this manner have configurations repeating irregular curves. If the elastics are visible through the sheet, the article will be disfigured. In addition, the inelastic regions have no adhesive distributed thereon and there is a possibility that, in the inelastic regions, the sheet might freely move and behave in an unintended manner. Eventually, for example when putting on or taking off the wearing article, the sheet in the inelastic regions might be formed with undesired gathers and part of the wearer's body might be caught by these gathers.

Solution to Problem

Some embodiments provide a wearing article which has a longitudinal direction and a transverse direction being orthogonal to the longitudinal direction. The wearing article includes a skin-facing surface, a non-skin-facing surface lying on the side opposite to the skin-facing surface, front and rear waist panels respectively defining front and rear waist regions, a crotch panel defining a crotch region lying between the front and rear waist regions, and an absorbent structure disposed on the skin-facing surface of at least the crotch panel.

The crotch panel has front and rear end portions extending in the transverse direction, lateral edge portions extending in the longitudinal direction, and a pair of leg sheets extending along the lateral edge portions. Each of the leg sheets includes a backing sheet and at least one leg elastic attached under tension to the backing sheet so as to extend in the longitudinal direction. Each of the leg sheets is attached to the skin-facing surfaces of the front and rear waist panels through first and second joint regions, respectively. Each of the leg sheets has an elastically contractible region lying between the first and second joint regions. Each of the leg sheets has elastically relaxed regions in end portions located outboard of the first and second joint regions in the longitudinal direction, and the elastically relaxed regions are formed on the surfaces thereof with gathers.

BRIEF DESCRIPTION OF DRAWINGS

The drawings illustrate specific embodiments of the present invention including optional and preferred embodiments.

DESCRIPTION OF EMBODIMENTS

The embodiments described below relates to a diaper as illustrated in FIGS. 1 through 10, including both optional and preferred features.

Figure 1:
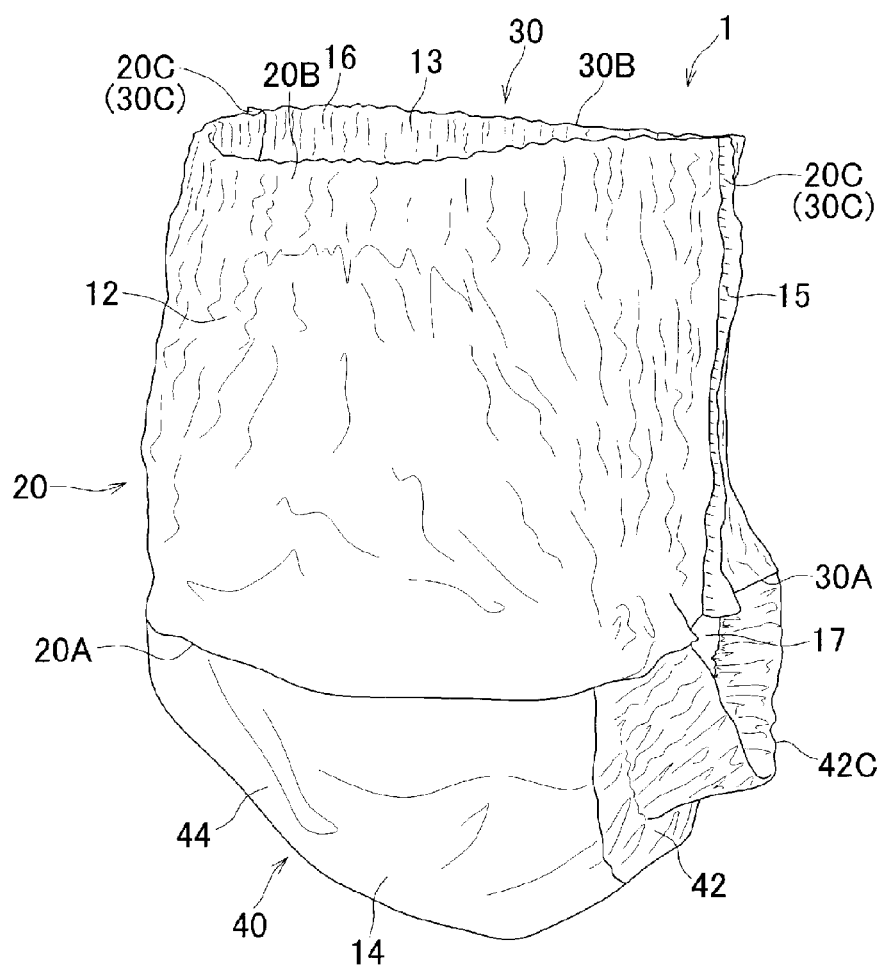
FIG. 1 is a perspective view of a diaper as an example of a wearing article according to some embodiments of the present invention.
Figure 2:
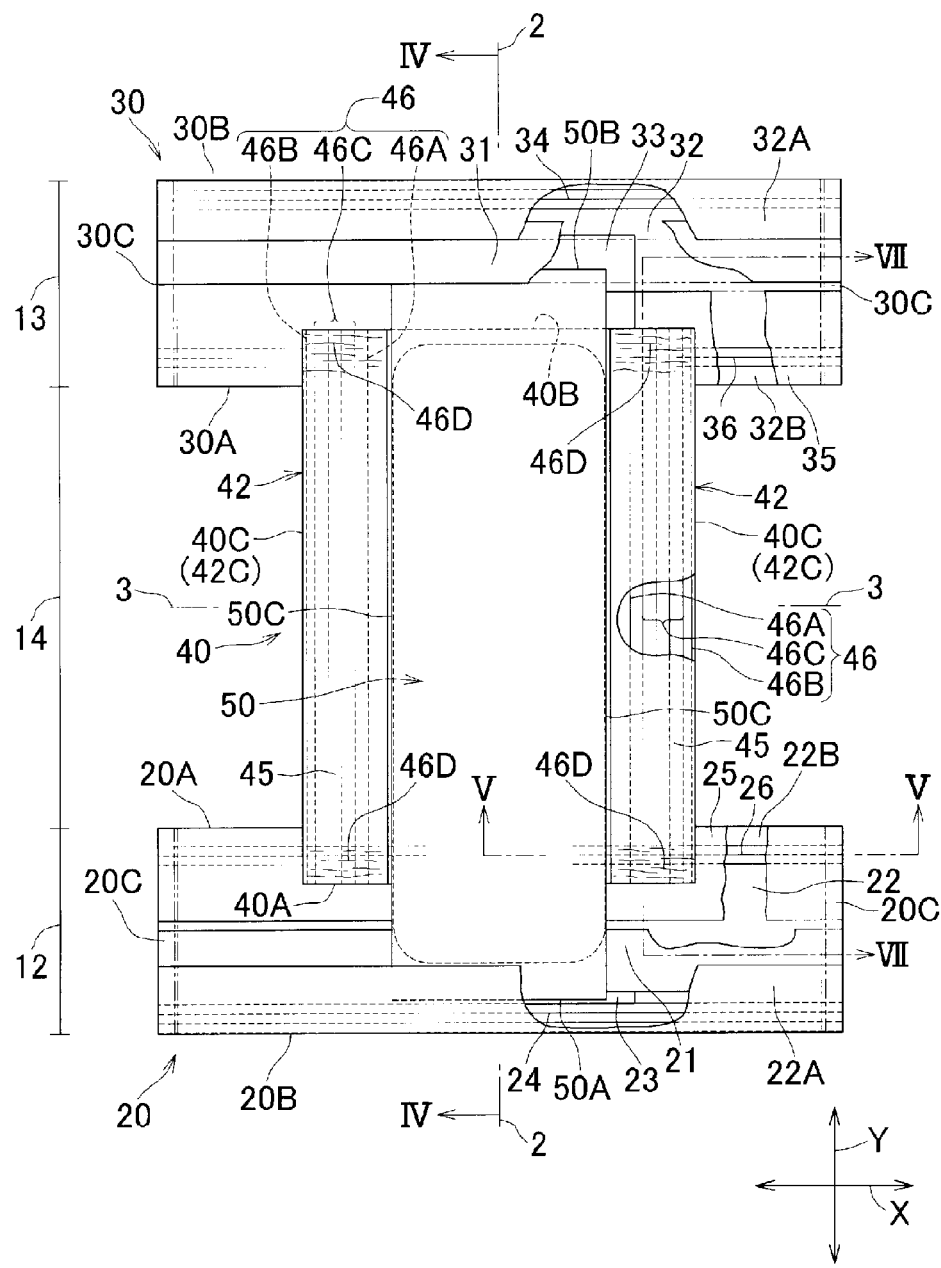
FIG. 2 is a partially cutaway developed plan view of the diaper developed in a longitudinal direction as well as in a transverse direction to the maximal elongation of respective leg elastics.

Referring to FIGS. 1 and 2, a diaper 1 as an example of wearing articles according to some embodiments of the present invention has a longitudinal direction Y in parallel to a longitudinal axis 2-2 and a transverse direction X in parallel to a transverse axis 3-3 and includes a skin-facing surface, a non-skin-facing surface lying on a side opposite to the skin-facing surface, a front waist region 12, a rear waist region 13, a crotch region 14 lying between the front and rear waist regions 12, 13, elastic front and rear waist panels 20, 30 defining the front and rear waist regions 12, 13, respectively, a crotch panel 40 attached to the skin-facing surface of the front and rear waist panels 20, 30, and an absorbent structure 50 located on the skin-facing surface of the crotch panel 40 so as to extend in the longitudinal direction Y.

The front and rear waist panels 20, 30 are respectively defined by inner end portions 20A, 30A, outer end portions 20B, 30B and lateral edge portions 20C, 30C. The lateral edge portions 20C and the lateral edge portions 30C are put flat and joined together along a series of seams 15 arranged at intervals in the longitudinal direction Y by, for example, heat sealing techniques such as hot embossing/debossing processing or ultrasonic sealing processing to form an annular elastic waist panel and to define a waist-opening 16 and a pair of leg-openings 17.

Figure 3:
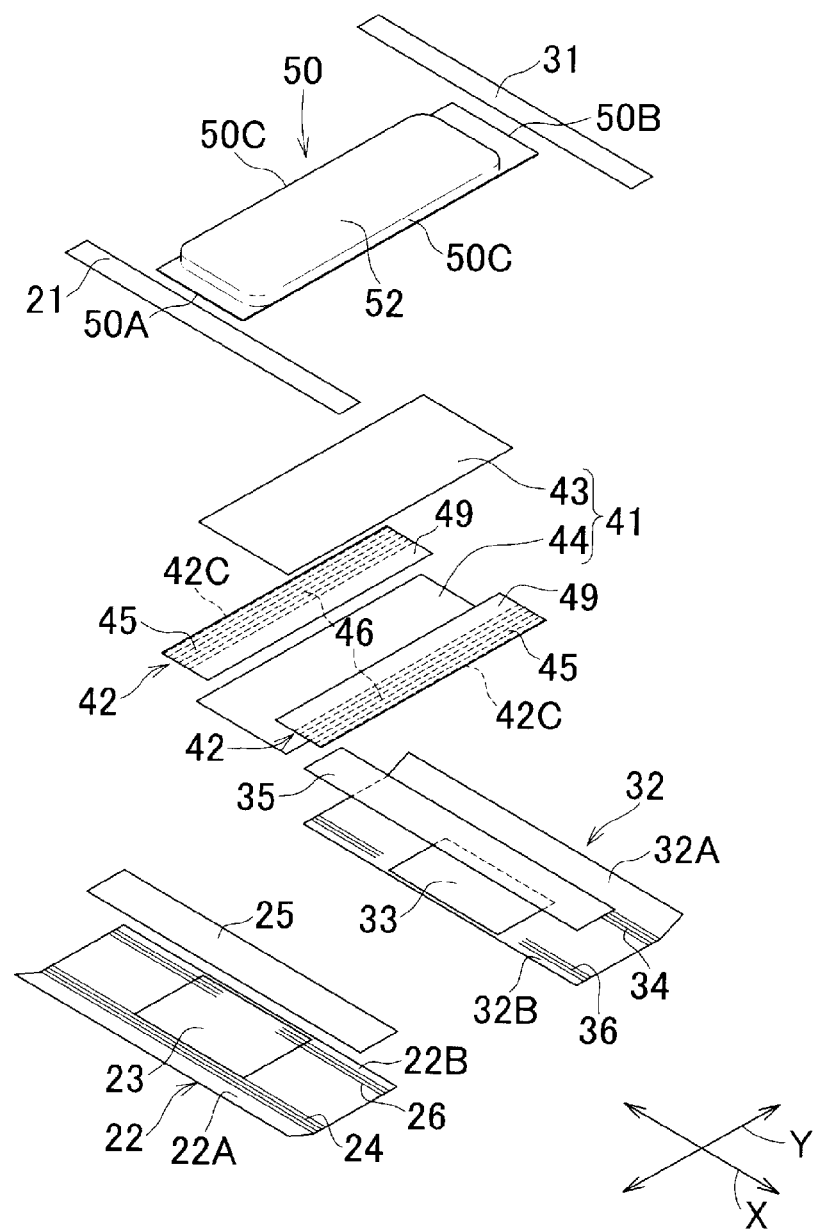
FIG. 3 is an exploded perspective view of the diaper.
Figure 4:
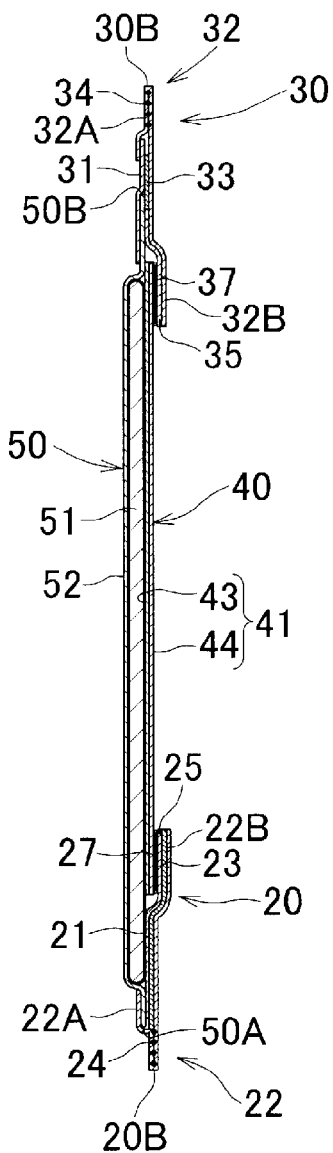
FIG. 4 is a sectional view taken along line IV-IV in FIG. 2.

Referring to FIGS. 2 through 4, in one example, the diaper 1 is substantially symmetrical about the longitudinal axis 2-2. The front and rear waist panels 20, 30 respectively may have interior waist sheets 21, 31 lying on the side of the skin-facing surface and exterior waist sheets 22, 32 lying on the side of the non-skin-facing surface. The exterior waist sheets 22, 32 respectively may have a width dimension in the longitudinal direction Y larger than that of the interior waist sheets 21, 31 and may extend outwardly in the longitudinal direction Y beyond inner and outer end edges of the interior waist sheets 21, 31. The interior waist sheets 21, 31 and the exterior waist sheets 22, 32 are respectively joined to each other through, for example, a hot melt adhesive distributed at least to respective one of the respective interior and exterior waist sheets or by heat sealing techniques.

Materials which may be used as the exterior waist sheets 22, 32 include, for example, an SMS (spunbonded/meltblown/spunbonded) fibrous nonwoven fabric, a spunbonded fibrous nonwoven fabric, an air-through fibrous nonwoven fabric, a plastic sheet, and a laminated sheet of one of the above-described fibrous nonwoven fabrics and the plastic sheet, each having a mass per unit area in a range of, for example, about 10 to about 30 g/m$^2$.

Materials which may be used as the interior waist sheets 21, 31 include various elastic fibrous nonwoven fabrics formed of, for example, a spunbonded fibrous nonwoven fabric, a meltblown fibrous nonwoven fabric, a heat-rolled fibrous nonwoven fabric, an SMS fibrous nonwoven fabric, an air-laid fibrous nonwoven fabric and an air-through fibrous nonwoven fabric, solely or in combination thereof. The elastic nonwoven fabrics may be formed, for example, from a polyethylene- or polyurethane-based elastomeric resin or polyethylene-, polypropylene-, polyester-based or acrylic thermoplastic resin. In this regard, an inelastic fibrous nonwoven fabric also may be used as material for the interior waist sheets 21, 31.

The exterior waist sheets 22, 32 may extend outwardly in the longitudinal direction Y beyond the respective outer end edges of the interior waist sheets 21, 31 to define fold regions 22A, 32A folded inwardly in the longitudinal direction Y and may extend toward the transverse axis 3-3 beyond the respective inner end portions of the interior waist sheets 21, 31 to define extension regions 22B, 32B. The fold regions 22A, 32A contain therein a plurality of thread, strand or string first and second waist elastics 24, 34 contractibly attached under tension. The first and second waist elastics 24, 34 may extend in the transverse direction X substantially over the entire range of each fold region 22A, 32A. The first and second waist elastics 24, 34 attached in this manner are particularly effective to keep the waist-opening 16 of the diaper 1 in place, thereby preventing body exudates such as urine from leaking beyond the waist line.

Preferably, the extension regions 22B, 32B of the exterior waist sheets 22, 32 extending toward the transverse axis 3-3 beyond the inner sheets 21, 31 are disposed thereon with elongate reinforcing sheets 25, 35 formed of fibrous nonwoven fabrics, and thread, strand or string third and fourth waist elastics 26, 36 are attached under tension with a hot melt adhesive between the reinforcing sheets 25, 35 and the extension regions 22B, 32B. The third and fourth waist elastics 26, 36 in vicinities of the longitudinal axis 2-2 form elastically relaxed regions. In order to form the elastically relaxed regions, for example, the respective portions of the third and fourth waist elastics 26, 36 predetermined to lie in the elastically relaxed regions may be left under no tension. Alternatively, for example, the contractility of the respective portions of the third and fourth waist elastics 26, 36 being under tension also in the regions which should be inelastic may be deprived or inhibited in these regions in order to form the elastically relaxed regions. The elastically relaxed regions formed in these manners are effective to prevent the absorbent structure 50 disposed on the longitudinal axis 2-2 from getting wrinkled, and the contractile force of the third and fourth waist elastics 26, 36 functions to keep the leg-openings 17 in close contact with the wearer's thighs, thereby preventing the leakage of body exudates such as urine.

As material for the first to fourth waist elastics, for example, elastic threads having a fineness in a range of about 310 to about 940 dtex and an elongation ratio of in a range of 2.0 to 3.5, may be used.

Between the interior waist sheets 21, 31 and the exterior waist sheets 22, 32, graphic display elements 23, 33 formed from a plastic sheet material may be located in respective central regions in the transverse direction X of the front and rear waist regions 12, 13. The graphic display elements 23, 33 may be printed on the non-skin-facing surface with, for example, graphics (not shown) which are visible externally.

The crotch panel 40 has front and rear end portions 40A, 40B extending in the transverse direction X and overlapping with the front and rear waist panels 20, 30 and lateral edge portions 40C extending in the longitudinal direction Y and includes a base sheet 41 lying in a central region as viewed in the transverse direction X and a pair of leg sheets 42 attached to lateral edge portions of the base sheet 41 wherein the leg sheets 42 function as leg barrier cuffs. The leg sheets 42 include backing sheets 49 and a plurality of leg elastics 46 extending in the longitudinal direction Y and attached under tension to the backing sheets 49 so as to leave elastically relaxed regions 42B (See FIGS. 6 and 7) at longitudinally opposite end portions 42D, 42E. The leg sheets 42 lie adjacent to the absorbent structure 50 and joined to the absorbent structure 50 through the base sheet 41. The front and rear end portions 40A, 40B of the crotch panel 40 are defined by the front and rear end portions of the base sheet 41 and the leg sheets 42 and the lateral edge portions 40C are defined by outer lateral edge portions 42C of the respective leg sheets 42. A dimension in the longitudinal direction Y of the crotch panel 40 may be smaller than a dimension in the longitudinal direction Y of the absorbent structure 50 and, in consequence, front and rear end portions 50A, 50B of the absorbent structure 50 lie outboard of the front and rear end portions 40A, 40B of the crotch panel 40 as viewed in the longitudinal direction Y (See FIG. 2).

The base sheet 41 includes an interior crotch sheet 43 lying on the side of the skin-facing surface and an exterior sheet 44 lying on the side of the non-skin-facing surface. As material for the interior and exterior crotch sheets 43, 44, various types of fibrous nonwoven fabrics or plastic films may be used. The interior crotch sheet 43 is preferably formed of a leakage-barrier plastic film. The exterior sheet 44 is preferably formed of a fibrous nonwoven fabric having a texture superior to that of a plastic film since the exterior sheet 44 constitutes part of the exterior surface of the diaper 1. The leg sheets 42 respectively may have inner lateral edge portions attached between the interior and exterior crotch sheets 43, 44.

Figure 5:
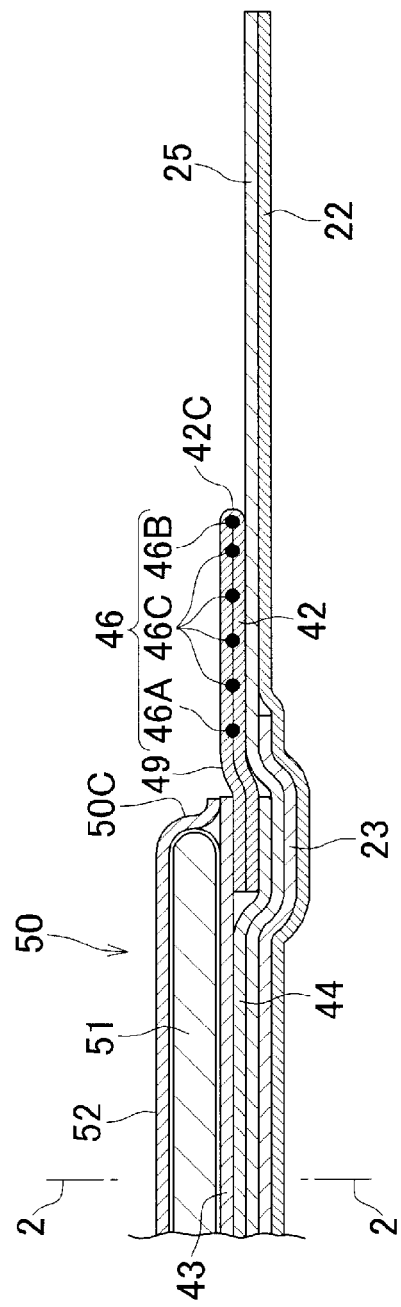
FIG. 5 is a sectional view taken along line V-V in FIG. 2.

Each of the leg sheets 42 preferably has a fold region 45 folded inwardly in the transverse direction X along the outer lateral edge portion 42C extending in the longitudinal direction Y and the plurality of thread, strand or string leg elastics 46 extending in the longitudinal direction Y attached within a sleeve or tube defined by the fold region 45 (See FIG. 5). As material for the leg elastics 46, for example, elastic threads having a fineness in a range of about 310 to about 620 dtex and an elongation ratio in a range of about 2.0 to about 3.0 may be used and these leg elastics 46 are contractibly attached under tension to the leg sheet 42 with a hot melt adhesive. The leg elastics 46 include an innermost leg elastic 46A which is closest to the longitudinal axis 2-2, i.e., lying on the innermost side as viewed in the transverse direction X, an outermost leg elastic 46B lying on the outermost side as viewed in the transverse direction X and intermediate leg elastics 46C lying between the innermost and outermost leg elastics. According to the embodiment exemplified in FIG. 5, the outermost leg elastic 46B lies on the outer lateral edge portion 42C and the leg sheet 42 is folded along the outermost leg elastic 46B so as to define the fold region 45. According to another embodiment, it is also possible to fold the leg sheet 42 along a line extending outside the outermost leg elastic 46B as viewed in the transverse direction X to define the fold region 45. In the latter case, the outermost leg elastic 46B is not present in the outer lateral edge portion 42C of the leg sheet 42 and, consequently, a texture of the outer lateral edge portion 42C is improved.

In the front waist panel 20, the innermost leg elastic 46A, the outermost leg elastic 46B and the intermediate leg elastics 46C intersect (or overlap) with the third waist elastics 26 extending in the transverse direction X. Consequently, the absorbent structure 50 is kept in close contact with the wearer's body under a contractile force of the third waist elastics 26, and a gap liable to induce a leakage of body exudates is unlikely to be formed between the wearer's body and the absorbent structure 50 even when the wearer's thighs move. In the rear waist panel 30, the fourth leg elastics 36 extending in the transverse direction X partially intersect (or overlap) with the outermost leg elastic 46B and the intermediate leg elastics 46C but do not intersect (or overlap) with the remaining intermediate leg elastics 46C and the innermost leg elastic 46A. Consequently, in the rear waist region 13, the contractile force of the leg elastics 46 does not excessively act on the absorbent structure 50 to form the absorbent structure 50 with cracks and/or wrinkles liable to induce a leakage of body exudates.

As used herein, "the leg elastics 46 intersect with the third and fourth waist elastics 26, 36" means that the reinforcing sheets 25, 35 to which the third and fourth waist elastics 26, 36 are attached under tension are joined to the leg sheets 42 to which the leg elastics 46 are attached under tension and, consequently, the leg elastics 46 are functionally coordinate with the third and fourth waist elastics 26, 36.

The crotch panel 40 has the absorbent structure 50 disposed on the skin-facing surface of the base sheet 41. The absorbent structure 50 has a longitudinally long pad configuration, front and rear end portions 50A, 50B and lateral edge portions 50C, and includes an absorbent core 51 extending in the longitudinal direction Y at least in the crotch region 14 and a bodyside liner 52 located on an absorbent surface of the absorbent core 51, i.e., on the skin-facing surface of the absorbent core 51. The front end portion 50A is attached to the interior waist sheet 21 of the front waist panel 20 with a hot melt adhesive. The rear end portion 50B is attached between the interior waist sheet 31 and the exterior waist sheet 32, more specifically, between the interior waist sheet 31 and the reinforcing sheet 35 of the rear waist panel 30 with a hot melt adhesive. An intermediate portion of the absorbent structure 50 defined between the front and rear end portions 50A, 50B is attached to the interior crotch sheet 43 of the crotch panel 40 with a hot melt adhesive. The front end portion 50A of the absorbent structure 50 is attached to the skin-facing surface of the interior waist sheet 21 and the interior waist sheet 21 which is elasticized and relatively flexible comes into direct contact with the wearer's skin, whereby texture is improved. The rear end portion 50B is attached between the interior waist sheet 31 and the exterior waist sheet 32 and, in consequence, the wearer's skin is protected against coming in direct contact with body exudates even when the body exudates diffuse from the crotch region 14 to a portion of the absorbent structure 50 lying in the rear waist region 13.

The absorbent core 51 may have a mass per unit area in a range of about 200 to about 800 g/m² and may include a core material of a mixture of fluff pulp, superabsorbent polymer particles (SAP) and optionally heat-sealable staple fibers and a liquid-permeable fibrous nonwoven fabric adapted to wrap the core material. Materials which may be used as the bodyside liner 52 include, for example, various types of fibrous nonwoven fabrics such as a liquid-permeable spunbonded nonwoven fabric or an SMS nonwoven fabric each having a mass per unit area in a range of about 10 to about 30 g/m².

Figure 6:
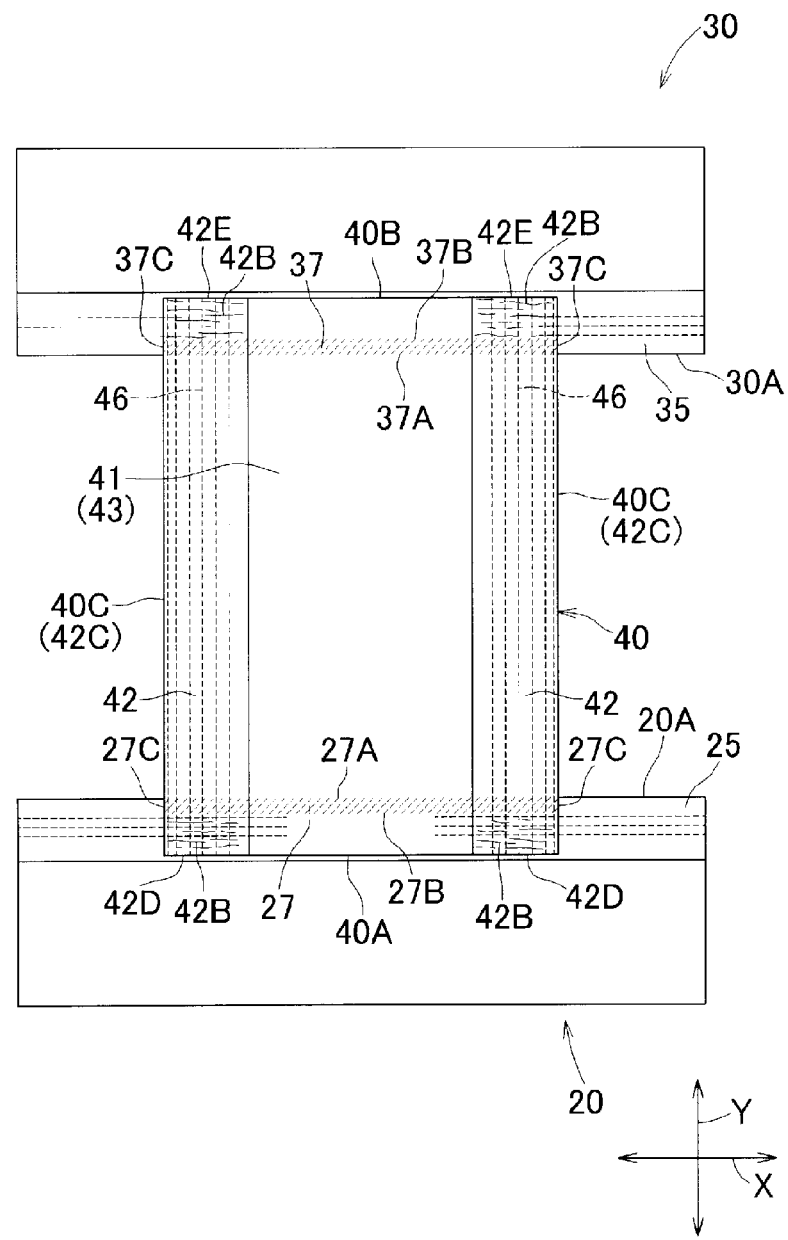
FIG. 6 is a schematic diagram illustrating a joint region.

Referring to FIG. 6, along the inner end portions 20A, 30A of the front and rear waist panels 20, 30, first and second joint regions 27, 37 in which inner portions adjacent to the front and rear end portions 40A, 40B of the crotch panel 40 are attached to the front and rear waist panels 20, 30 extend in the transverse direction X. The first and second joint regions 27, 37 are formed of a hot melt adhesive distributed to the reinforcing sheets 25, 35 and respectively have lateral edge portions 27C, 37C extending in the longitudinal direction Y and inner end portions 27A, 37A and outer end portions 27B, 37B extending in the transverse direction X substantially in parallel to each other. The respective lateral edge portions 27C, 37C of the first and second joint regions 27, 37 overlap with the outer lateral edge portions 42C of the respective leg sheets 42, i.e., the lateral edge portions 40C of the crotch panel 40. Of the end edge portions of the first and second joint regions 27, 37, the inner end portions 27A, 37A closer to the transverse axis 3-3 lie adjacent to the inner end portions 20A, 30A of the front and rear waist panels 20, 30. As used herein, "lie adjacent to" means that the hot melt adhesive is spaced apart from the inner end portions 20A, 30A by a distance assuring the hot melt adhesive to be reliably prevented from running over the inner end portions 20A, 30A considering a processing accuracy in the step of distributing the hot melt adhesive. Dimensions in the longitudinal direction Y of the first and second joint regions 27, 37, i.e., respective distances between the inner end portions 27A, 37A and the outer end portions 27B, 37B may be appropriately selected and, for example, these distances may be set to 50% or less of elastically relaxed regions 42B to be described later.

Figure 7:
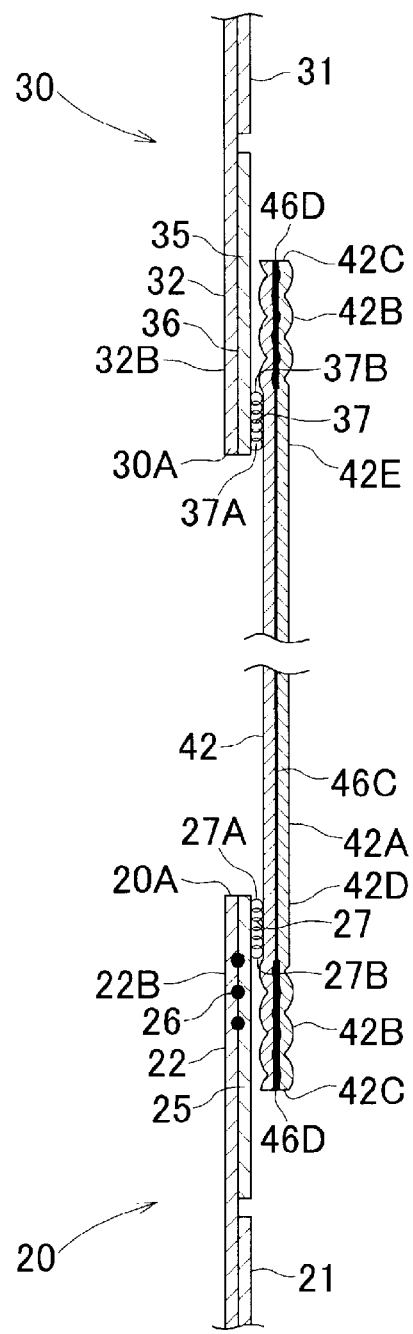
FIG. 7 is a schematic diagram corresponding to a sectional view taken along line VII-VII in FIG. 2, illustrating a cross-section of an elastically relaxed region.

Referring to FIG. 7, the end portions 42D, 42E opposite in the longitudinal direction Y of the leg sheets 42 having the leg elastics 46 contractibly attached under tension thereto are attached to the reinforcing sheets 25, 35 through the first and second joint regions 27, 37, respectively, and thereupon the portions of the leg elastics 46 extending between respective end portions 46D of the leg elastics 46 and the respective outer end portions 27B, 37B of the first and second joint regions 27, 37 (i.e., end portions of the leg sheets 42 located outboard of the first and second joint regions 27, 37 in the longitudinal direction Y) are released from the state under tension. Upon release from the state under tension, the leg elastics 46 contract not in an irregularly curved configuration but rectilinearly contract since the leg elastics 46 have been contractibly attached under tension to the leg sheets 42. In this manner, the elastically relaxed regions 42B are formed along portions of the leg elastics 46 having been released from the state under tension and respective surfaces of these elastically relaxed regions 42B are formed with gathers due to contraction of the leg elastics 46 having been released from the state under tension. As used herein "an elastically relaxed region of a leg sheet" is a region that has elasticity and is in a relaxed state so that elasticity of the elastically relaxed region does not affect other elements of the wearing article outside the leg sheet. Meanwhile, between the inner end portions 27A, 37A of the first and second joint regions 27, 37, the absorbent structure 50 having a relatively high stiffness inhibits a contraction of the leg elastics 46 and consequently forms an elastically contractible region 42A.

In the elastically relaxed regions 42B, the leg elastics 46 rectilinearly contract and the diaper 1 is unlikely to be disfigured due to the contraction of the leg elastics 46. In addition, the surfaces of these elastically relaxed regions 42B are formed with gathers providing a cushioning effect and softly come into contact with the wearer's skin, and the wearer's skin is unlikely to suffer from an oppressive feeling due to the contraction of elastic materials. Meanwhile, the leg elastics 46 rectilinearly extend in the elastically relaxed regions 42B and consequently a configuration of the respective elastically relaxed regions 42B may be sufficiently stabilized and these elastically relaxed regions 42B is unlikely to unintentionally behave. In other words, the diaper 1 is disposed with an elastic composite sheet which is unlikely to be disfigured and/or unintentionally behave in the elastically relaxed regions 42B, contrary to a case utilizing a snap-back method. In addition, the leg elastics 46 are attached to the leg sheets 42 also in the elastically relaxed regions 42B and, in consequence, the leg elastics 46 are unlikely to fall off the elastically relaxed regions 42B under the effect of tensile force acting on the elastically contractible regions 42A, contrary to a case utilizing a snap-back method.

Figure 8:
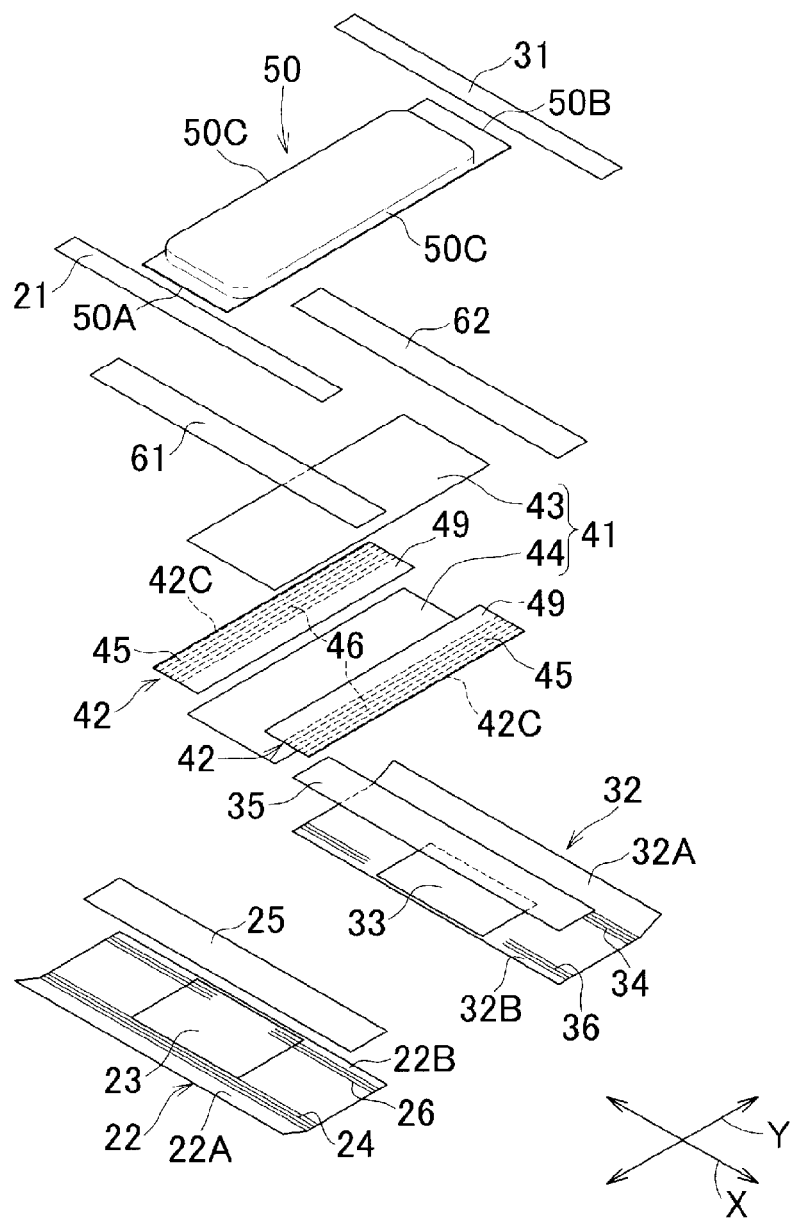
FIG. 8 is an exploded perspective view of a diaper according to some embodiments.
Figure 9:
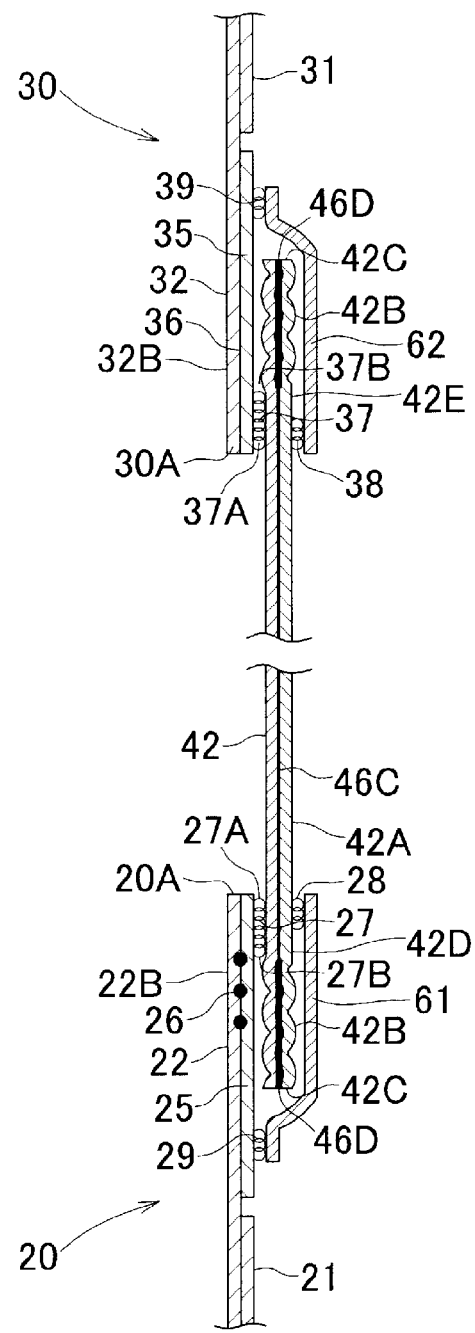
FIG. 9 is a schematic diagram similar to FIG. 7, illustrating a cross-section of an elastically relaxed region according to some embodiments.

According to some embodiments, as illustrated in FIGS. 8 and 9, cover sheets 61, 62 adapted to cover the elastically relaxed regions 42B are attached to the front and rear waist panels 20, 30. FIG. 9 is a schematic diagram similar to FIG. 7, illustrating a cross-section of the elastically contractible region 42A and the elastically relaxed regions 42B. The leg sheet 42 is attached to the front and rear panels 20, 30 exclusively in the first and second joint regions 27, 37. In other words, the elastically relaxed region 42B is not directly attached to the front and rear waist panels 20, 30. Cover sheets 61, 62 are respectively attached to third and fourth joint regions 28, 38 formed on the leg sheet 42 so as to face each other across the leg sheet 42, and to fifth and sixth joint regions 29, 39 formed on the reinforcing sheets 25, 35 so as to lie outboard of the outer lateral edge portion 42C of the leg sheet 42 as viewed in the longitudinal direction Y. The first and second joint regions 27, 37 are formed in the same manner as in the embodiments described with respect to FIGS. 1 through 7, and the third to sixth joint regions 28, 38, 29, 39 are formed of a hot melt adhesive. Preferably, lateral edge portions extending in the longitudinal direction Y in the cover sheets 61, 62 are also attached to the front and rear waist panels 20, 30.

Referring to FIG. 9, the elastically relaxed regions 42B are free from distribution of any hot melt adhesive, and a stiffness of these elastically relaxed regions 42B is unlikely to be increased due to adhesive. Consequently, a flexibility of the elastically relaxed regions 42B may be maintained even after these regions 42B have been covered with the cover sheets 61, 62. In addition, the leg elastics 46 rectilinearly contract to form gathers which provide a cushioning effect and the wearer's skin is unlikely to be uncomfortably compressed due to the contraction of the elastic materials. Beside such advantageous effects, the cover sheets 61, 62 function to prevent the outer lateral edge portions 42C from being unintentionally curled inwardly of the diaper 1 when the diaper 1 is put on the wearer's body.

As another arrangement, it is possible to lengthen a dimension in the longitudinal direction Y of the interior waist sheets 21, 31 sufficiently to respectively cover the elastically relaxed regions 42B without use of the separately prepared cover sheets 61, 62. It is also possible to lengthen a dimension in the longitudinal direction Y of the exterior waist sheets 22, 32 sufficiently to cover the elastically relaxed regions 42B with the portions of the exterior waist sheets 22, 32 respectively folded inwardly. While FIG. 8 exemplifies a case in which the cover sheets 61, 62 respectively extend between the lateral edge portions 20C, 30C of the front and rear waist panels 20, 30, it is not essential for the cover sheets 61, 62 to extend fully between the lateral edge portions 20C, 30C so long as the elastically relaxed regions 42B may be covered with the respective cover sheets 61, 62. Furthermore, while the case in which the leg elastics 46 are continuously attached to the backing sheets 49 or the leg sheets 42, it is also possible to attach the leg elastics 46 to the backing sheets 49 and/or the leg sheets 42 at some intervals.

Figure 10:
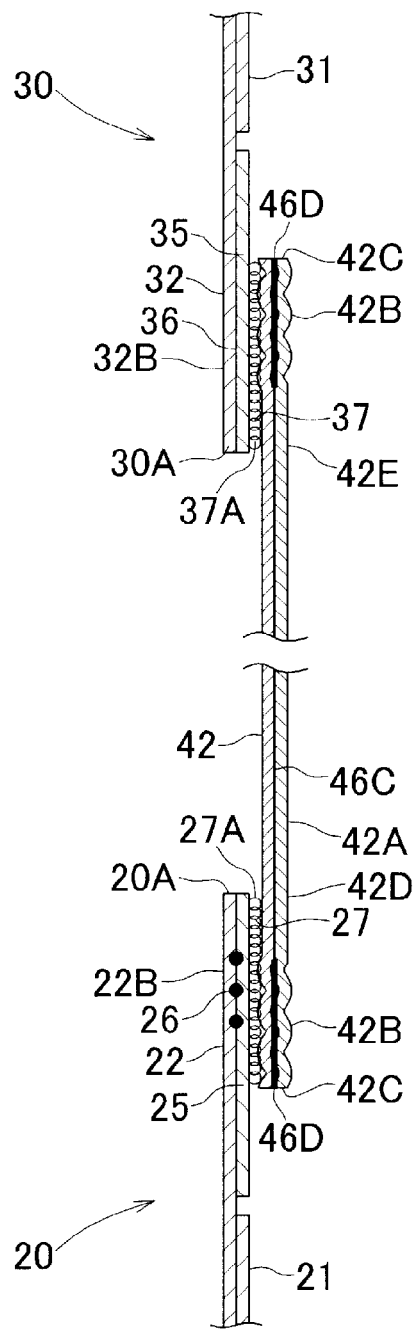
FIG. 10 is a schematic diagram similar to FIG. 7, illustrating a cross-section of an elastically relaxed region according to some embodiments.

According to some embodiments, as illustrated in FIG. 10, substantially entire surfaces of the elastically relaxed regions 42B are respectively attached to the front and rear waist panels 20, 30. The configuration in FIG. 10 is obtained by attaching the elastically relaxed regions 42B already formed with gathers, e.g., as in the configuration of FIG. 7, to the reinforcing sheets 25, 35 with a hot melt adhesive. According to the configuration in FIG. 10, substantially entire surfaces of the respective elastically relaxed regions 42B are directly attached to the front and rear waist panels 20, 30, and consequently the elastically relaxed regions 42B are unlikely to be unintentionally curled inwardly of the diaper 1 in the course of putting the diaper 1 on the wearer's body. Furthermore, even when a stiffness of the elastically relaxed regions 42B is increased due to distribution of a hot melt adhesive, the elastically relaxed regions 42B are formed with gathers which provide a cushioning effect, and the wearer's skin is unlikely to be uncomfortably compressed due to the contraction of the elastic materials. In this way, the elastically relaxed regions softly come into contact with the wearer's skin.

The constituent elements of the diaper 1 are not limited to those described in the specification but other various types of materials widely used in the relevant technical field, or to be developed, may be used without limitation unless otherwise stated. The terms "first", "second", "third" and "fourth" used herein are merely to distinguish similar elements or similar positions.

The disclosure described above may be arranged in at least one or more of the following features.

A wearing article 1 having a longitudinal direction Y and a transverse direction X being orthogonal to the longitudinal direction Y, including: a skin-facing surface, a non-skin-facing surface lying on a side opposite to the skin-facing surface; front and rear waist panels 20, 30 respectively defining front and rear waist regions 12, 13; a crotch panel 40 defining a crotch region 14 lying between the front and rear waist regions 12, 13; and an absorbent structure 50 disposed on the skin-facing surface of at least the crotch panel 40 so as to extend in the longitudinal direction Y, wherein:

the crotch panel 40 has front and rear end portions 40A, 40B extending in the transverse direction X, lateral edge portions 40C extending in the longitudinal direction Y, and a pair of leg sheets 42 extending along the lateral edge portions 40C;

each of the leg sheets 42 includes a backing sheet 49 and at least one leg elastic 46 attached under tension to the backing sheet so as to extend in the longitudinal direction Y;

each of the leg sheets 42 is attached to the skin-facing surfaces of the front and rear waist panels 20, 30 through first and second joint regions 27, 37, respectively;

each of the leg sheets 42 has an elastically contractible region 42A lying between the first and second joint regions 27, 37; and each of the leg sheets 42 has elastically relaxed regions 42B in end portions located outboard of the first and second joint regions 27, 37 in the longitudinal direction Y, and the elastically relaxed regions are formed on surfaces thereof with gathers.

The present disclosure may include at least the following embodiments, which may be taken in isolation or in combination with one another:

(1) The front and rear waist panels 20, 30 are respectively disposed with cover sheets 61, 62 adapted to cover the respective elastically relaxed regions 42B which are not directly attached to the front and rear waist panels 20, 30.

(2) The cover sheets 61, 62 are not attached to the elastically relaxed regions 42B.

(3) The elastically relaxed regions 42B are directly attached to the front and rear waist panels 20, 30.

(4) The elastically relaxed regions 42B are not directly attached to the front and rear waist panels 20, 30.

(5) At least one of the front and rear waist panels 20, 30 has a waist sheet 21, 31, 22, 32 folded inwardly to cover the elastically relaxed regions 42B.

(6) Each of the leg sheets 42 includes a plurality of leg elastics 46 interposed and attached under tension between two layers of the respective doubled up backing sheet 49.

In the elastically relaxed regions in the wearing article according to some embodiments of the present invention, end portions of the leg elastics contractibly attached under tension to the leg sheets are released from the state under tension after the leg sheets having the leg elastics contractibly attached under tension thereto have been attached to the front and rear waist panels. Upon release from the state under tension, the leg elastics rectilinearly contract, not in a configuration repeating irregular curves, since the leg elastics have been attached under tension. Consequently, it is ensured that the elastically relaxed regions are protected against being disfigured due to contraction of the leg elastics and, in addition, the leg sheets are formed on the surfaces thereof with gathers providing a cushioning effect to protect the wearer's skin against uncomfortable compression due to the contraction of elastic materials, assuring the elastically relaxed regions to come into comfortable direct or indirect contact with the wearer's skin. Further, the leg elastics rectilinearly extending in the elastically relaxed regions sufficiently stabilize the configurations of the elastically relaxed regions to prevent these regions from behaving in an unintentional manner.

This application claims the benefit of Japanese Applications Nos. 2012-218690 and 2013-142160 the entire disclosures of which are incorporated by reference herein.

The invention claimed is:

1. A wearing article having a longitudinal direction and a transverse direction being orthogonal to the longitudinal direction, the wearing article comprising:
    a skin-facing surface;
    a non-skin-facing surface lying on a side opposite to the skin-facing surface;
    front and rear waist panels respectively defining front and rear waist regions;
    a crotch panel defining a crotch region lying between the front and rear waist regions; and
    an absorbent structure disposed on the skin-facing surface of at least the crotch panel, wherein:
    the crotch panel has
        front and rear end portions extending in the transverse direction,
        lateral edge portions extending in the longitudinal direction, and
        a pair of leg sheets extending along the lateral edge portions;
    each of the leg sheets includes a backing sheet and at least one leg elastic attached under tension to the backing sheet so as to extend in the longitudinal direction;
    each of the leg sheets is attached to the skin-facing surfaces of the front and rear waist panels through first and second joint regions, respectively;
    each of the leg sheets has an elastically contractible region lying between the first and second joint regions;
    each of the leg sheets has elastically relaxed regions in end portions located outboard of the first and second joint regions in the longitudinal direction, and the elastically relaxed regions are formed on surfaces thereof with gathers; and
    the front and rear waist panels are respectively disposed with cover sheets adapted to cover the respective elastically relaxed regions which are not directly attached to the front and rear waist panels.

2. The wearing article according to claim 1, wherein the cover sheets are not attached to the elastically relaxed regions.

3. A wearing article having a longitudinal direction and a transverse direction being orthogonal to the longitudinal direction, the wearing article comprising:
    a skin-facing surface;
    a non-skin-facing surface lying on a side opposite to the skin-facing surface;
    front and rear waist panels respectively defining front and rear waist regions;
    a crotch panel defining a crotch region lying between the front and rear waist regions; and
    an absorbent structure disposed on the skin-facing surface of at least the crotch panel, wherein:
    the crotch panel has
        front and rear end portions extending in the transverse direction,
        lateral edge portions extending in the longitudinal direction, and
        a pair of leg sheets extending along the lateral edge portions;
    each of the leg sheets includes a backing sheet and at least one leg elastic attached under tension to the backing sheet so as to extend in the longitudinal direction;
    each of the leg sheets is attached to the skin-facing surfaces of the front and rear waist panels through first and second joint regions, respectively;
    each of the leg sheets has an elastically contractible region lying between the first and second joint regions;
    each of the leg sheets has elastically relaxed regions in end portions located outboard of the first and second joint regions in the longitudinal direction, and the elastically relaxed regions are formed on surfaces thereof with gathers; and
    at least one of the front and rear waist panels has a waist sheet folded inwardly to cover the elastically relaxed regions.

4. A wearing article having a longitudinal direction and a transverse direction being orthogonal to the longitudinal direction, the wearing article comprising:

a skin-facing surface;
a non-skin-facing surface lying on a side opposite to the skin-facing surface;
front and rear waist panels respectively defining front and rear waist regions;
a crotch panel defining a crotch region lying between the front and rear waist regions; and
an absorbent structure disposed on the skin-facing surface of at least the crotch panel, wherein:
the crotch panel has
 front and rear end portions extending in the transverse direction,
 lateral edge portions extending in the longitudinal direction, and
 a pair of leg sheets extending along the lateral edge portions;
each of the leg sheets includes a backing sheet and at least one leg elastic attached under tension to the backing sheet so as to extend in the longitudinal direction;
each of the leg sheets is attached to the skin-facing surfaces of the front and rear waist panels through first and second joint regions, respectively;
each of the leg sheets has an elastically contractible region lying between the first and second joint regions;
each of the leg sheets has elastically relaxed regions in end portions located outboard of the first and second joint regions in the longitudinal direction, and the elastically relaxed regions are formed on surfaces thereof with gathers;
each of the leg sheets includes a plurality of leg elastics interposed and attached under tension between two layers of the respective doubled up backing sheet; and
at least one of the front and rear waist panels has a waist sheet folded inwardly to cover the elastically relaxed regions.

\* \* \* \* \*